(12) United States Patent
Aoki et al.

US006797501B2

(10) Patent No.: US 6,797,501 B2
(45) Date of Patent: Sep. 28, 2004

(54) PROTEIN TYROSINE PHOSPHATASE PTP20 AND RELATED PRODUCTS AND METHODS

(75) Inventors: Naohita Aoki, Nagoya (JP); Axel Ullrich, Martinsried (DE)

(73) Assignee: Max-Planck-Gessellschaft zur Fonderung de Wissenschaften E.V., Munich (DE)

(*) Notice: Subject to any disclaimer, the term of this patent is extended or adjusted under 35 U.S.C. 154(b) by 0 days.

(21) Appl. No.: 10/243,687

(22) Filed: Sep. 16, 2002

(65) Prior Publication Data

US 2003/0073120 A1 Apr. 17, 2003

Related U.S. Application Data

(62) Division of application No. 09/430,626, filed on Oct. 29, 1999, now Pat. No. 6,482,605, which is a division of application No. 08/951,260, filed on Oct. 16, 1997, now Pat. No. 6,004,791.
(60) Provisional application No. 60/030,860, filed on Nov. 13, 1996.

(30) Foreign Application Priority Data

Jun. 17, 1997 (WO) ................................ PCT/IB97/00946

(51) Int. Cl.⁷ ............................ C12N 9/12; C12N 1/20; C12N 15/00; C07H 21/04
(52) U.S. Cl. ...................... 435/194; 435/195; 435/196; 435/252.3; 435/320.1; 536/23.2; 530/300; 530/350
(58) Field of Search ................................ 435/194, 196, 435/252.3, 320.1, 195; 536/23.2; 530/300, 350

(56) References Cited

U.S. PATENT DOCUMENTS

| 4,376,110 | A | | 3/1983 | David et al. | .................... 435/5 |
| 4,945,050 | A | | 7/1990 | Sanford et al. | .......... 435/172.1 |
| 5,283,173 | A | | 2/1994 | Fields et al. | .................... 435/6 |
| 5,589,375 | A | * | 12/1996 | Ullrich et al. | ............... 435/325 |

FOREIGN PATENT DOCUMENTS

| WO | WO 93/09236 | 5/1993 |
| WO | WO 94/23039 | 10/1994 |
| WO | 96/18738 | 6/1996 |
| WO | WO 96/18738 | 6/1996 |
| WO | 97/00946 | 6/1997 |
| WO | 97/35019 | 9/1997 |
| WO | WO 97/48723 | 12/1997 |

OTHER PUBLICATIONS

Cheng et al. Blood 88 : 1156–67 (1996).*
Abe et al., "Molecular Characterization of a Novel Metabotropic Glutamate Receptor mGluR5 Coupled to Inositol Pohosphate/Ca$^{2+}$ Signal," *J. Biol. Chem.* 267(19):13361–13368 (1992).
Keane, et al., "Proceedings of the American Association for Cancer Research Annual Meeting" 36, 1995. 60:358, Mar. 22, 1995.
Dosil, et al., "Cloning and Characterization of Fetal Liver Phosphatase 1, a Nuclear Protein Tyrosine Phosphatase Isolated From Hematopoietic Stem Cells", *Blood*, vol 88, No 12, pp 4510–4525, Dec. 15, 1996.
*EMBI Accession No. U49853*, "Mus Musculus Protein Tyrosine Phosphatase, mRNA, Complete cds." Mar. 27, 1996.
EMBL Accession number U55057, Rel. 47 created on May 28, 1996 Mus musculus receptor protein tyrosine phosphatase–lambda (ptp–lambda) mRNA. XP002064044 see the whole document.
Wang, H. Et Al.: "Characterization Of PcP–2, A Novel Receptor Protein Tyrosine Phosphatase Of The Mam Domain Family" *Oncogene*, vol. 12, No. 12, Jun. 20, 1996, pp. 2555–2562, Xp002064033 See The Whole Document.
Kim Y. W. Et. Al: "Characterization Of The Pest Family Protein Tyrosine Phosphatase Bdp1" *Oncogene*, vol. 13, No. 10, Nov. 21, 1996, pp. 2275–2279, Xp002034272 See The Whole Document.
Winfield, S. L. Et Al.: "Identification Of Three Additional Genes Contiguous To The Glucocerebrosidase Locus On Chromosome 1q21: Implications For Gaucher Disease" *Genome Research.*, vol. 7, No. 10, 1997, Ing Harbor Laboratory Press Us, pp. 1020–1026, Xp002064037 See The Whole Document.
Hanes, J.J. Et. Al.: "Characterization By Cdna Cloning Of Two New Human Protein Kinases: Evidence By Sequence Comparison For A New Family of Mammalian Protein Kinases" *Journal Of Biological Chemistry* (Microfilms), vol. 244, No. 5, 1994, Md Us, pp. 665–672, Xp002054038 See The Whole Document.
Becker, W. Et. Al.: "Cdna Cloning And Characterization Of Rat Clk3, A Lammer Kinase Predominantly Expressed In Testis" *Biochim. Biophy. Acta*, vol. 1312, No. 1, Jun. 5, 1996, Orlando, Fl Us, pp. 63–67, Xp002064040 See The Whole Document.

(List continued on next page.)

*Primary Examiner*—Tekchand Saidha
(74) *Attorney, Agent, or Firm*—Beth A. Burrous; Foley & Lardner LLP

(57) ABSTRACT

The present invention relates to a novel polypeptide, PTP20, and to nucleic acid molecules encoding the polypeptide. The invention also relates to nucleic acid molecules encoding portions of the phosphatase, nucleic acid vectors containing PTP20 related nucleic acid molecules, recombinant cells containing such nucleic acid vectors, polypeptides purified from such recombinant cells, antibodies to such polypeptides, and methods of identifying compounds that bind PTP20 or abrogate its interactions with natural binding partners. Also disclosed are methods for diagnosing abnormal conditions in an organism with PTP20 related molecules or compounds.

17 Claims, No Drawings

OTHER PUBLICATIONS

Johnson, K.W. & Smith, K.A.: "Molecular Cloning Of A Novel Human Cdc2/CDC28–Like Protein" *Journal of Biological Chemistry (Microfilms)*, vol. 266, No. 6, Feb. 25, 1991, MD US, pp. 3402–3407, XP002064041 See The Whole Document.

Kharitonenkov, A. Et Al.: "A Family Of Proteins That Inhibit Signalling Through Tyrosine Kinase" *Nature.*, vol. 386, Mar. 13, 1997, London Gb, pp. 181–186, Xp002064043 See The Whole Document.

Nayler et al., "Characterization and comparison of four serine– and arginine–rich (SR) protein kinases," *Biochem. J.* 326:693–700 (1997).

Hillier, et al., (May 18, 1995). Accession No. R54222. Genbank database. The WashU–Merck EST Project.

Ota, et al., "A Gene Encoding A Putative Tyrosine Phosphatase Suppresses Lethality of an N–End Rule–Dependent Mutant", *Proc. Natl. Acad. Sci.*, 89,2355–2359, 1992.

Ausubel et al., Current Protocols in Molecular Biology, *Greene Publishing Associates and Wiley Interscience, NY* (1989) (Table of Contents Only).

Bardford et al., "Crystal Structure of Human Protein Tyrosine Phosphatase 1B," *Science* 263:1397–1403 (1994).

Bayer et al., "The Avidin–Biotin Complex in Affinity Cytochemistry," *Methods in Enzymol*, 62:308–319 (1979).

Beckman et al., "An Adhesive Domain Detected in Functionally Diverse Receptors", *Trends Biochem. Sci.* 18:40–41 (1993).

Benoist et al., "In Vivo Sequence Requirements of the Sv40 Early Promoter Region," *Nature* 290, 304–310 (1981).

Blaschuk et al., "Identification of a Conserved Region Common to Cadherins and Influenza Strain A Hemagglutinins" *J. Mol. Biol.* 211, 679–682 (1990).

Bollon et al., "DNA Transformation Efficiency of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Academic Press*, 19, 265–274 (1982).

Brinster et al., "Factors Affecting the Efficiency of Introducing Foreign DNA into Mice by Microinjecting Eggs," *Proc. Natl. Acad. Sci., USA* 82:4438–4442 (1985).

Broach, "The Yeast Plasmid 2μ Circle," in *The Molecular Biology of the Yeast Saccharomyces: Life Cycle and Inheritance*, Cold Spring Harbor Laboratory, Cold Spring Harbor, NY, pp. 445–470 (1981).

Broach, "The Yeast Plasmid 2μ Circle," *Cell* 28:203–204 (1982).

Brown–Shimer et al., "Molecular cloning and chromosome mapping of the human gene encoding protein phosphotyrosyl phosphatase IB," *Proc. Natl. Acad. Sci. USA* 87:5148–5152 (1990).

Bullock et al., "Techniques in Immunocytochemistry," vol. 1 (1982), vol. 2 (1983), vol. 3 (1985) (Table of Contents Only).

Campbell, "Monoclonal Antibody Technology: Laboratory Techniques in Biochemistry and Molecular Biology," 13, (1984) (Table of Contents Only).

Capecchi, "Altering the Genome by Homologous Recombination," *Science* 244(1) 1288–1292 (1989).

Capecchi, "High Efficiency Transformation by Direct Microinjection of DNA into Cultured Mammalian Cells," *Cell* 22:479–488 (1980).

Cenatiempo, Prokaryotic gene expression in vitro: transcription–translation coupled systems, *Biochimie* 68, 505–515 (1986).

Chard, "An Introduction to Radioimmunoassay and Related Techniques," *Elsevier Science* (1986) (Table of Contents Only).

Chater et al., "Streptomyces φC3 1–Like Phages: Cloning Vectors, Genome Changes and Host Range," *Sixth International Symposium on Actinomycetes Biology*, 45–52 (1986).

Chen et al., "High–Efficiency Transformation of Mammalian Cells by Plasmid DNA," *Mol. and Cell. Biol.* 7(8):2745–2752 (1987).

Chirgwin et al., "Isolation of Biologically Active Ribonucleic Acid from Sources Enriched in Ribonuclease" *Biochemistry* 18, 5294–5299 (1979).

Chu et al., "Etectroporation for the Efficient Transfection of Mammalian Cells with DNA," *Nucl. Acids Res.* 15(3) 1311–1326 (1987).

Clossek et al, "Cloning, Characterization, and Differential Expression of MDK2 and MDK5, Two Novel Receptor Tyrosine Kinases of the eck/eph Family" *Oncogene* 11:2085–2095 (1995).

Colwill et al., "The Clk/Sty Protein Kinase Phosphorylates SR Splicing Factors and Regulates Their Intranuclear Distribution" *EMBO J.* 15:265–275 (1996).

Cool et al., "DNA Isolated from a Human T–cell Library Encodes a Member of the Protein–tyrosine–phosphatase Family," *Proc. Natl. Acad. Sci. USA* 86, 5257–5761 (1989).

Cunningham et al., "Neural Cell Adhesion Molecule: Structure, immunoglobulin–Like Domains, Cell Surface Modulation, and Alternative RNA Splicing" *Science* 236, 799–806 (1987).

Curiel et al., "Gene Transfer to Respiratory Epithelial Cells via the Receptor–mediated Endocytosis Pathway," *Am. J. Respir. Cell. Mol. Biol.* 6, 247–252(1992).

Dignam et al., "Accurate Transcription Initiation by RNA Polymerase II in a Soluble Extract from Isolated Mammalian Nuclei," *Nucl. Acids Res.* 11(5) 1475–1489 (1983).

Dingwall et al., "Nuclear Targeting Sequences a Consensus?" *TIBS* 16, 478–481 (1991).

Dreborg et al., "Ch. 10—The chemistry and standardization of allergens," *Handbook of Experimental Immunology—vol. 1: Immunochemistry, 4th Ed., Blackwell Scientific Publications*, 10, 10.1 –10.28 (1986).

Duncan et al., "Alternative Splicing of STY, a Nuclear Dual Specificity Kinase" *J. Biol. Chem.* 270:21524 (1995).

Eaton et al., "Construction and Characterization of an Active Factor VIII Variant Lacking the Central One–Third of the Molecule" *Biochemistry* 25(26) 8343–8347 (1986).

Engvall et al., "Enzyme–Linked Immunosorbent Assay, ELISA. III. Quantitation of the Specific Antibodies by Enzyme–Labeled Anti–Immunoglobulin in Antigen–Coated Tubes," *J. Immunol.* 109, 129–135 (1972).

Feigner et al., "Lipofection: A Highly Efficient, Lipid–mediated Dna–transfection Procedure," *Proc. Natl. Acad. Sci. USA* 84:7413–7417(1987).

Felgner et al., "Cationic Liposome–mediated Transfection," *Nature* 337, 387–388 (1989).

Fendly et al., "Characterization of Murine Monoclonal Antibodies Reactive to Either the Human Epidermal Growth Factor Receptor or HER2/neu Gene Product," *Cancer Research* 50, 1550–1558 (1990).

Field et al., Cloning and Characterization of CAP, the S. Cerevisiae Gene Encoding the 70 kd Adenylyl Cyclase–Associated Protein *Cell* 61:319–327 (1990).

Flores et al., "Nuclear Localization of sthe PEP Protein Tyrosine Phosphatase" *Mol. Cell. Biol.* 14:4938–4946 (1994).

Fry et al., "New Insights into Protein–tyrosine Kinase Receptor Signaling Complexes," *Protein Science* 2:1785–1797 (1993).

Garton et al., A.J. and Tonics, N.K., PTP–PEST: a protein tyrosine phosphatase regulated by serine phosphorylation. *EMBO J.* 13:3763–3771 (1994).

Gilman et al., "Isolation of a sigma–28–specific promoters from *Bacillus subtilis* DNA," *Gene* 32, 11–20(1984).

Glick et al., "Factors affecting the expression of foreign proteins in *Escherichia coli*," *Journal of Industrial Microbiology* 1,277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18, 415–441 (1984).

Hamer et al., "Regulation In Vivo of a Cloned Mammalian Gene: Cadmium Induces the Transcription of a Mouse Metallothionein Gene in SV40 Vectors," *J. of Mol. and Applied Genetics* 1, 273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63, 1099–1112 (1990).

Hedley et al., "An Amino Acid Sequence Motif Sufficient for Subnuclear Localization of an Arginine/Serine–rich Splicing Factor" *Proc. Natl. Acad. Sci. USA* 92:11524–11528 (1995).

Houdebine et al., "Transgenesis in Fish," *Experientia* 47, 891–897 (1991).

Howell et al., "STY, a Tyrosine–Phosphorylationing Enzyme with Sequence Homology to Serine/Threonine Kinases" *Mol and Cell Biol.* 11(1) 568–572 (1991).

Hurby et al., "Applications of Synthetic Peptides: Antisense Peptides" in *Synthetic Peptides: A User's Guide*, edited by Gregory A. Grant, W.H. Freeman, NY, pp. 289–307 (1992).

Innis et al., "A Guide to Methods and Applications," Academic Press (1990) (Table of Contents Only).

Izaki, *Jpn J. Bacteriol.* 33:729–742 (1978).

Jansen et al., "Immunotoxins: Hybrid Molecules Combining High Specificity and Potent Cytotoxicity," *Immunolo. Rev.* 62, 185–216 (1982).

Jasny, "Insect Viruses Invade Biotechnology," *Science* 238, p. 1653 (1987).

Jiang et al., "The α Subunit of Merpron A" *J. of Biol. Chem.* 267:9185–9193 (1992).

John et al., "Plasmids as Epidemologic Markers in Nosocomial Gram–Negative Bacilli: Experience at a University and Review of the Literature," *Rev. Infect. Dis.* 8(5) 693–704 (1986).

Johnston et al., "Isolation of the Yeast Regulatory Gene Ga14 and Analysis of its Dosage Effects on the Galactose/melibiose Regulon," *Proc. Natl. Acad. Sci. USA* 79:6971–6975 (1982).

Joyner et al., "Production of a Mutation In Mouse En–2 Gene by Homologous Recombination in Embryonic Stem Cells," *Nature* 338, 153–156 (1989).

Kappes et al., "Human Class II Major Histocompatibility Complex Genes and Proteins" *Ann. Rev. Biochem.* 57, 991–1028 (1988).

Kasprzak et al., "Location of a Contact Site Between Acting and Myosin in the Three–Dimensional Structure of the Acto–S1 Complex," *Biochemistry* 28, 9230–9238 (1989).

Kendall et al., "Plasmid Transfer in *Streptomyces lividans*: Identification of a kil–k0r System Associated with the Transfer Region of P1J101," *J. of Bacteriology* 169(9) 4177–4183 (1987).

Killen et al., "Specific Killing of Lymphocytes that Cause Experimental Autoimmune Myasthenia Gravis by Ricia Toxin–Acetylcholine Receptor Conjugates," *J. of Immunol.* 133(5) 2549–2553 (1984).

Kozak, "Compilation and Analysis of Sequences Upstream from the Translational Start Site in Eukaryotic mRNAs," *Nucleic Acids Research* 12(2) 857–872 (1984).

Kozak et al., "An Analysis of 5'–noncoding Sequences from 699 Vertebrate Messenger RNAs," *Nucl. Acids Res.* 15(20) 8125–8148 (1987).

Lammers et al., "Differential Activities of Protein Tyrosine Phosphatases in Intact Cells," *J. Biol Chem.* 268, 22456–22462 (1993).

Lechner et al., "ERK6, A Mitogen–activated Protein Kinase Involved in C2C12 Myoblast Differentiation" *Proc. Natl. Acad. Sci. USA* 93:4355–4359 (1996).

Lutz et al., "The Distribution of Two hnRNP–Associated Proteins Defined by a Monoclonal Antibody Is Altered in Heat–Shocked HeLa Cells" *Exp. Cell Res.* 175, 109–124 (1988).

Malissen et al., "Nucleotide Sequence of a Light Chain Gene of the Mouse I–A Subregion: $A\beta^{d}$" *Science* 221:750–754 (1983).

Matviw et al., "Identification of a Human cDNA Encoding a Protein That Is Structurally and Functionally Related to the Yeast Adenylyl Cyclase–Associated CAP Proteins" *Mol. Cell Biol.* 12(11) 5033–5040 (1992).

Mauro et al., "Homophilic and Heterophilic Binding Activities of Nr–CAM, a Nervous System Cell Adhesion Molecule" *J. Cell Biol.* 119, 191–202 (1992).

McKnight, "Functional Relationships between Transcriptional Control Signals of the Thymidine Kinase Gene of Herpes Simplex Virus," *Cell* 31, 355–365 (1982).

Millaner et al., "Glioblastoma Growth Inhibited In Vivo by a Dominant–negative Flk–1 Mutant," *Nature* 367:576–579 (1994).

Miller et al., "An Insect Baculovirus Host–Vector System for High–Level Expression of Foreign Genes," *Genetic Engineering: Principles and Methods*, edited by Setlow et al., Plenum Press, 8:277–298 (1986).

Miller and Rosman, "Improved Retroviral Vectors for Gene Transfer and Expression," *BioTechniques* 7(9) 982–990 (1989).

Miller, "Human gene therapy comes of age," *Nature* 357, 455–460(1992).

Mizuno et al., "Developmental Regulation of Gene Expression for the MPTPδ Isoforms in the Central Nervous System and the Immune System" *FEBS* 355, 223–228 (1994).

Nayler et al. "SAF–B Protein Couples Transcription and Pre–Mrna Splicing to SAR/MAR Elements" *Nucl. Acid. Res.* 26(15) 3542–2549 (1998).

Okayama et al., "A cDNA Cloning Vector That Permits Expression of cDNA Inserts in Mammalian Cells," *Mol. and Cell Biol.* 3, 280–289 (1983).

Pear et al., "Product ion of high–titer helper–free retroviruses by transient transfection," *Proc. Natl. Acad. Sci. USA* 90:8392–8396 (1993).

Puissant et al., "An Improvement of sthe Single–Step Method of RNA Isolation by Acid Guanidinium Thiocyanate–Phenol–Chloroform Extraction" *Biotechniques* 8(2) 148–149 (1990).

Pursel et al., "Genetic Engineering of Livestock," *Science* 244, 1281–1288 (1989).

Redemann et al., "Anti–Oncogenic Activity of Signalling–Defective Epidermal Growth Factor Receptor Mutants," *Mol. and Cell. Biol.* 2(2) 491–498 (1992).

Rogers et al., "Amino Acid Sequences Common to Rapidly Degraded Proteins: The PEST Hypothesis" *Science* 234:364–368 (1986).

Rubin, "*Drosophila melanogaster* as an Experimental Organism," *Science* 240, 1453–1459 (1988).

Sanger et al., "DNA Sequencing with Chain–terminating Inhibitors," *Proc. Natl. Acad. Sci. USA* 74, 5463–5467 (1977).

Silver et al., "Amino Terminus of the Yeast Gal4 Gene Product Is Sufficient for Nuclear Localization," *Proc. Natl. Acad. Sci. USA* 81, 5951–5955 (1984).

Simons et al., "Gene Transfer Into Sheep" *Bio/Technology* 6:179–183 (1988).

Smith et al., "Single–step Purification of Polypeptides Expressed in *Escherichia Coli* as Fusions with Glutathione S–transferase" *Gene*, 67:31–40 (1988).

St. Groth et al., "Production of Monoclonal Antibodies: Strategy and Tactics," *J. Immunol. Methods* 35:1–21 (1980).

Stein–Geriach et al., "Protein–tyrosine Phosphate 1D Modulates Its Own State of Tyrosine Phosphorylation" *J. Biol. Chem.* 270:24635–24637 (1995).

Sternberger et al. "The Unlabeled Antibody Enzyme Method of Immunohistochemistry" *J. Histochem. Cytochem.* 18(5) 315–333 (1970).

Stuckey et al., "Crystal Structure of Yersinia Protein Tyrosine Phospatase at 2.5 Å and the Complex with Tungstate" *Nature* 370:571–575 (1994).

Su et al., "The Crystal Structure of a Low–Molecular–Weight Phosphostyroisine Protein Phosphatase" *Nature* 370, 575–578 (1994).

Takagi et al., "The A5 Antigen, a Candidate for the Neuronal Recognition Molioculem Has Homologies to Complement Components and Coagulation Factors" *Neuron.* 7:295–307 (1991).

Thomas et al., "Structural Modification of Acidic Fibroblast Growth Factor Alter Activity, Stability, and Heparin Dependence" *Ann. NY Acad. Sci.* 8–17 (1991).

Tijssen, *Practice and Theory of Enzyme Immunoassays: Laboratory Techniques in Biochemistry and Molecular Biology*, vol. 15, Elsevier Science Publishers, Amsterdam, The Netherlands (Table of Contents Only) (1985).

Ullrich et al., "Rat Insulin Genes: Construction of Plasmids Containing the Coding Sequences" *Science* 196:1313–1319 (1977).

Ulmanen et al., "Transcription and Translation of Foreign Genes in *Bacillus subtilis* by the Aid of a Secretion Vector," *J. of Bacteriology* 162, 176–182 (1985).

Vogel et al., "Activation of a Phosphotyrosine Phosphatase by Tyrosine Phosphorylation," *Science* 259:1611–1614 (1994).

Von Jeijne, "A New Method for Predicting Signal Sequence Cleavage Sites" *Nucleic Acids Res.* 14(11) 4683–4690 (1986).

Ward et al., "Construction and Characterisation of a Series of Multi–copy Promoter–probe Plasmid Vectors for Streptomyces Using the Aminoglycoside Phosphotransferase Gene from Tn5 as Indicator," *Mol. Gen. Genet.* 203, 468–478 (1986).

Yamauchi et al., "Identificatiuon of the Major SHPTP2–binding Protein That is Tyrosine–phosphorylated in Response to Insulin" *J. Biol. Chem.* 270:17716–17722 (1995).

Yamauchi et al., "Epidermal Growth Factor Induced Association of the SHPTP2 Protein Tyrosine Phosphatase with a 115–kDa Phosphotyrosine Protein" *J. Biol. Chem.* 270:14871–14874 (1995).

Yang et al., "In Vivo and In Vitro Gene Transfer to Mammalian Somatic Cells by Particle Bombardment," *Proc. Natl. Acad. Sci. USA* 87, 9568–9572 (1990).

Yun et al., "The Doa Locus Encodes a Member of a New Protein Kinase Family and is Essential for Eye and Embryonic Development in Drosophila Melanogaster" *Genes Dev.* 8, 1160–1173 (1994).

Zahler et al., "SR Proteins: A Conserved Family of Pre–mRNA Splicing Factors" *Genes Dev.* 6, 837–847 (1992).

Zelicof et al., "Molecular Cloning and Characterization of a Rat Homolog of CAP, The Adenylyl Cyclase–Associated Protein From Saccharomyces Cervisiae" *J. of Biol. Chem.* 268(18) 13448–13453 (1993).

Zhang, et al., "Dissecting the Catalytic Mechanism of Protein Tyrosin Phosphatases" *Proc. Natl. Acad. Sci. USA* 91:1624–1627 (1994).

Abe eet al., "Molecular Characterization of a Novel Metabotropic Glutamate Receptor mGluR5 Coupled to Inositol Phosphate/$Ca^{2+}$ Signal," *J. Biol. Chem.* (1992), 267(19):13361–13368.

Aoki et al., "The Novel protein–tyrosin phosphatase PTP20 is a positive regulator of PC12 cell nueronal differentiation," *J. Biol. Chem.* (1996), 271:19422–29426.

Ben–David et al., "A mammalian protein kinase with potential for serine/threonine and tyrosine phosphorylation is related to cell cycle regulators," *EMBO Journal*, (1991) 10:317–325.

Chao, "Growth Factor Signalling: Where is the Specificity?" *Cell* (1992) 68:995–997.

Cheng et al., "A Novel Protein Tyrosine Phosphatase Expressed in LOCD34HISCAHI Hematopoietic Progenitor Cells," *Blood* (1996) 88:1156–1167.

Chomczynski and Sacchi, "Single–Step Method of RNA Isolation by Acid Guanidinium Thiocyanate–Phenol–Chloroform Extraction," *Analytical Biochemistry* (1987) 162:156–159.

Gossen et al., "Tight Control of Gene Expression in Mammalian Cells by Tetracycline–Responsive Promotors," *Proc. Natl. Acad. Sci. USA* (1992) 89:5547–5551.

Hempstead et al., "Expression of the v–crk Oncogene Product in PC12 Cells Results in Rapid Differentiation by both Nerve Growth Factor and Epidermal Growth Factor–Dependent Pathways," *Mol. Cell. Biol.* (1994) 14_1964–1971.

Kohler and Milstein, "Continuous cultures of fused cells secreting antibody of predefined specificity," *Nature* (1975) 256:495–497.

Krueger and Saito, "A human transmembrane protein–tyrosine–phosphatase, PTPζ, is expressed in brain and has an N–terminal receptor domain homologous to carbonic anhydrases," *Proc. Natl. Acad. Sci. USA* (1992) 89:7417–7421.

Kunkel, "Rapid and efficient site–specific mutagenesis without phenotypic selection," *Proc. natl. Acad. Sci. USA* (1985), 82:488–492.

Kyte and Doolittle, "A Simple Method for Displaying the Hydropathic Character of a Protein," *J. Mol. Biol.*, (1982) 157:105–132.

Matthews et al., "Characterization of Hematopoietic Intracellular Protein Tyrosine Phosphatases: Description of a Phosphatase Containing an SH2 Domain and Another Enriched in Proline–, Glutamic Acid–, Serine– and Theonine–Rich Sequences," *Mol. Cell, Biol.* (1992) 12:2396–2405.

Mayer et al., "A novel viral oncogene with structural similarity to phospholipase C," *Nature* (1988), 332:272–275.

Nelson, Detection of Acridinium Esters by Chemiluminescence, *Nonisotopic DNA Probe Techniques*, ed. Larry J. Krinka, (San Diego: Academic Press, Inc. (1992), pp. 275–310.

Obermeier et al., "Tyrosine 785 is a major determinant of Trk–substrate Interaction," *The EMBO Journal* (1993) 12(3):933–941.

\* cited by examiner

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
        (A) LENGTH: 2226 base pairs
        (B) TYPE: nucleic acid
        (C) STRANDEDNESS: single
        (D) TOPOLOGY: linear (ii) MOLECULE TYPE: cDNA to tRNA (xi) SEQUENCE DESCRIPTION: SEQ ID NO: 1:

```
GAATTCCGGC ACGAGGCGGG TTGCAGTATG AGTCGCCAAT CGGACCTAGT GAGGAGCTTC    60

TTGGAGCAGC AGGAGGCCCG GGACCACCGG AAGGGGGCAA TCCTCGCCCG TGAGTTCAGC   120

GACATTAAGG CCCGCTCAGT GGCTTGGAAG ACTGAAGGTG TGTGCTCCAC TAAAGCCGGC   180

AGTCAGCAGG GAAACTCAAA GAAGAACCGC TACAAAGACG TGGTACCGTA TGATGAGACG   240

AGAGTCATCC TTTCCCTGCT CCAGGAGGAA GGACACGGAG ATTACATTAA TGCCAACTTC   300

ATCCGGGGCA CAGATGGAAG CCAGGCCTAC ATTGCGACGC AAGGACCCCT GCCTCACACT   360

CTGTTGGACT TCTGGCGCCT GGTTTGGGAG TTTGGAATCA AGGTGATCTT GATGGCCTGT   420

CAGGAGACAG AAAATGGACG GAGGAAGTGT GAACGCTACT GGGCCCAGGA GCGGGAGCCT   480

CTACAGGCCG GGCCTTTCTG CATCACCCTG ACAAAGGAGA CAGCACTGAC TTCGGACATC   540

ACTCTCAGGA CCCTCCAGGT TACATTCCAG AAGGAATCCC GTCCTGTGCA CCAGCTACAG   600

TACATGTCTT GGCCGGACCA CGGGGTTCCC AGCAGTTCCG ATCACATTCT CACCATGGTG   660

GAGGAGGCCC GTTGCCTCCA AGGACTTGGA CCTGGACCCC TCTGTGTCCA CTGCAGTGCT   720

GGCTGTGGAC GAACAGGTGT CTTGTGTGCT GTTGATTACG TGAGGCAGTT GCTTCTGACT   780

CAGACAATCC CACCCAATTT CAGCCTCTTT GAAGTGGTCC TGGAGATGCG GAAACAGCGA   840

CCTGCAGCGG TGCAGACAGA GGAGCAGTAC AGGTTCCTGT ACCACACAGT GGCTCAGCTA   900

TTCTCCCGCA CTCTCCAGAA CAACAGTCCC CTCTACCAGA ACCTCAAGGA GAACCGCGCT   960

CCAATCTGCA AGGACTCCTC GTCCCTCAGG ACCTCCTCAG CCCTGCCTGC CACATCCCGC  1020

CCACTGGGTG GCGTTCTCAG GAGCATCTCG GTGCCTGGGC CACCGACCCT TCCCATGGCT  1080

GACACTTACG CTGTGGTGCA GAAGCGTGGC GCTTCCGGCA GCACAGGGCC GGGCACGCGG  1140

GCGCCCAACA GCACGGACAC CCCGATCTAC AGCCAGGTGG CTCCACGTAT CCAGCGGCCC  1200

GTGTCACACA CCGAAAACGC GCAGGGGACA ACGGCACTGG GCCGAGTTCC TGCGGATGAA  1260

AACCCTTCCG GGCCTGATGC CTATGAGGAA GTAACAGATG GAGCGCAGAC TGGTGGGCTA  1320

GGCTTCAACT TGCGCATTGG AAGACCTAAA GGGCCACGGG ATCCTCCAGC GGAGTGGACA  1380

CGGGTGTAAT GAGTGCTGTA CCAGTTCCAG CCTGTCACTC AGTGGTGGCT GGGCGACTGC  1440

AACCCCCATG CTGCTGTGTG CTGTCTTATG TATGAGTGGG ACTCATGGGC CTGAATCAAA  1500

ATAAAAGTTT CTCAGGGTAG AAAAAAACAA ATAGGGACTT TGGCCAGTGG TTATAGCAGT  1560

CAAAGCCAGG GGCTAGGAGG GGTAAGTGGG GGAGGTGGTG GATCTACTCT GAGAAAGTTT  1620

AGGAAAGCAC ATCAAGAGTG AGCATCGCCA CTCTTCTCCC CATACACCTA CTGGAAAGTG  1680

CACCCCAGAC AGAGTCCTAA CTTGACAGTG CACCTCAGAC AGGTCGCTAC CTGGATGGAC  1740

ATGCTGGCCC TACAGCTAGA GACATGTCTA ATTAGATCCT CATGTAAACT TGCAATGAGC  1800
```

```
TAGAAAGATC TCCGTCTGGT CAGGGAAATG GATCACCTAG TCAGGTAAAT AGTGTGCCAT    1860

CCAGAAGACA GAACTGCAAG ATACCGTCTT TCTCAAAATG GAAGAAAATA GATCCTCAAG    1920

AATAAATGTA TGTACAATGC TCTACGCCCT GATCCTGCCC TGCCTCACTG CCATAATGTC    1980

ACAAACAAGT CAGGGTCTAT ATGACAGTTG TTCATCTAGT CAGTCCTGAC TGTGGCCTCT    2040

GCAGGCTCAG ATAGTGCCTT CTGCAGACTC TTGGAATGCC CGTCTTGAAC TTGATGAAAG    2100

CTTCTACCGG GAACTTGTAA ACATCATTAA AATTATTAAT GTAGAATTCA ATAAAGAGTG    2160

GGTCAAAAAC TCAAAAAAAA AAAAAAAAAA AAAAAAAAAC TCGAGAGTAC TTCTAGAGCG    2220

GGCGGG                                                              2226

(2) INFORMATION FOR SEQ ID NO: 2:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:  "Xaa" in positions 3 and 5 stand
             for an unspecified amino acid.

(xi) SEQUENCE DESCRIPTION: SEQ ID NO: 2:

Phe Trp Xaa Met Xaa Trp
 1               5

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:  "Xaa" in position 6 stands for
             either Ser, Ile or Val.

(xi) SEQUENCE DESCRIPTION: SEQ ID NO: 3:

His Cys Ser Ala Gly Xaa Gly
 1               5

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 4:

CTCTGTGTCC ACAGCAGTGC TGGCTGT                                         27

(2) INFORMATION FOR SEQ ID NO: 5:

(i) SEQUENCE CHARACTERISTICS:
        (A) LENGTH: 59 base pairs
        (B) TYPE: nucleic acid
        (C) STRANDEDNESS: single
        (D) TOPOLOGY: linear
```

-continued (xi) SEQUENCE DESCRIPTION: SEQ ID NO: 5:

ATGAATTCGC CACCATGCAT CACCATCACC ATCACAGTCG CCAATCGGAC CTAGTGAGG    59

(2) INFORMATION FOR SEQ ID NO: 6:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (xi) SEQUENCE DESCRIPTION: SEQ ID NO: 6:

ATCTCGAGTT ACACCCGTGT CCACTCCGCT GGAGGATC    38

(2) INFORMATION FOR SEQ ID NO: 7:

(i) SEQUENCE CHARACTERISTICS:
      (A) LENGTH: 453 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 7:

```
Met Ser Arg Gln Ser Asp Leu Val Arg Ser Phe Leu Glu Gln Gln Glu
 1               5                  10                  15

Ala Arg Asp His Arg Lys Gly Ala Ile Leu Ala Arg Glu Phe Ser Asp
            20                  25                  30

Ile Lys Ala Arg Ser Val Ala Trp Lys Thr Glu Gly Val Cys Ser Thr
        35                  40                  45

Lys Ala Gly Ser Gln Gln Gly Asn Ser Lys Lys Asn Arg Tyr Lys Asp
     50                  55                  60

Val Val Pro Tyr Asp Glu Thr Arg Val Ile Leu Ser Leu Leu Gln Glu
65                  70                  75                  80

Glu Gly His Gly Asp Tyr Ile Asn Ala Asn Phe Ile Arg Gly Thr Asp
                85                  90                  95

Gly Ser Gln Ala Tyr Ile Ala Thr Gln Gly Pro Leu Pro His Thr Leu
            100                 105                 110

Leu Asp Phe Trp Arg Leu Val Trp Glu Phe Gly Ile Lys Val Ile Leu
        115                 120                 125

Met Ala Cys Gln Glu Thr Glu Asn Gly Arg Arg Lys Cys Glu Arg Tyr
    130                 135                 140

Trp Ala Gln Glu Arg Glu Pro Leu Gln Ala Gly Pro Phe Cys Ile Thr
145                 150                 155                 160

Leu Thr Lys Glu Thr Ala Leu Thr Ser Asp Ile Thr Leu Arg Thr Leu
                165                 170                 175

Gln Val Thr Phe Gln Lys Glu Ser Arg Pro Val His Gln Leu Gln Tyr
            180                 185                 190

Met Ser Trp Pro Asp His Gly Val Pro Ser Ser Asp His Ile Leu
        195                 200                 205

Thr Met Val Glu Glu Ala Arg Cys Leu Gln Gly Leu Gly Pro Gly Pro
    210                 215                 220

Leu Cys Val His Cys Ser Ala Gly Cys Gly Arg Thr Gly Val Leu Cys
225                 230                 235                 240

Ala Val Asp Tyr Val Arg Gln Leu Leu Leu Thr Gln Thr Ile Pro Pro
                245                 250                 255

Asn Phe Ser Leu Phe Glu Val Val Leu Glu Met Arg Lys Gln Arg Pro
```

-continued

```
                260                 265                 270
Ala Ala Val Gln Thr Glu Glu Gln Tyr Arg Phe Leu Tyr His Thr Val
            275                 280                 285

Ala Gln Leu Phe Ser Arg Thr Leu Gln Asn Asn Ser Pro Leu Tyr Gln
            290                 295                 300

Asn Leu Lys Glu Asn Arg Ala Pro Ile Cys Lys Asp Ser Ser Ser Leu
305                 310                 315                 320

Arg Thr Ser Ser Ala Leu Pro Ala Thr Ser Arg Pro Leu Gly Gly Val
                325                 330                 335

Leu Arg Ser Ile Ser Val Pro Gly Pro Pro Thr Leu Pro Met Ala Asp
                340                 345                 350

Thr Tyr Ala Val Val Gln Lys Arg Gly Ala Ser Gly Ser Thr Gly Pro
            355                 360                 365

Gly Thr Arg Ala Pro Asn Ser Thr Asp Thr Pro Ile Tyr Ser Gln Val
        370                 375                 380

Ala Pro Arg Ile Gln Arg Pro Val Ser His Thr Glu Asn Ala Gln Gly
385                 390                 395                 400

Thr Thr Ala Leu Gly Arg Val Pro Ala Asp Glu Asn Pro Ser Gly Pro
                405                 410                 415

Asp Ala Tyr Glu Glu Val Thr Asp Gly Ala Gln Thr Gly Gly Leu Gly
            420                 425                 430

Phe Asn Leu Arg Ile Gly Arg Pro Lys Gly Pro Arg Asp Pro Pro Ala
            435                 440                 445

Glu Trp Thr Arg Val
450
```

PROTEIN TYROSINE PHOSPHATASE PTP20 AND RELATED PRODUCTS AND METHODS

RELATED APPLICATIONS

This application is a divisional of U.S. patent application Ser. No. 09/430,626, filed Oct. 29, 1999, now U.S. Pat. No. 6,482,605, which in turn is a divisional of U.S. patent application Ser. No. 08/951,260, filed Oct. 16, 1997, now U.S. Pat. No. 6,004,791, which in turn claims priority to PCT Application No. PCT/IB97/00946, filed Jun. 17, 1997 and U.S. Provisional Patent Application Serial No. 60/030, 860, filed Nov. 13, 1996, all of which are incorporated by reference herein in their entirety.

INTRODUCTION

The present invention relates generally to a newly identified protein tyrosine phosphatase and related products and methods.

BACKGROUND OF THE INVENTION

The following description of the background of the invention is provided to aid in understanding the invention, but is not admitted to describe or constitute prior art to the invention.

Cellular signal transduction is a fundamental mechanism whereby extracellular stimuli are relayed to the interior of cells and subsequently regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins.

Enzymes that mediate phosphorylation of cellular effectors generally fall into two classes. The first class consists of protein kinases which transfer a phosphate moiety from adenosine triphosphate to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases and protein phosphatases are generally divided into two groups—receptor and non-receptor type proteins. Most receptor-type protein tyrosine phosphatases contain two conserved catalytic domains, each of which encompasses a segment of 240 amino acid residues. Saito et al., 1991, *Cell Growth and Diff.* 2:59–65. Receptor protein tyrosine phosphatases can be subclassified further based upon the amino acid sequence diversity of their extracellular domains. Saito et al., supra; Krueger et al., 1992, *Proc. Natl. Acad. Sci. USA* 89:7417–7421.

Protein kinases and protein phosphatases are also typically divided into three classes based upon the amino acids they act upon. Some catalyze the addition or hydrolysis of phosphate on serine or threonine only, some catalyze the addition or hydrolysis of phosphate on tyrosine only, and some catalyze the addition or hydrolysis of phosphate on serine, threonine, and tyrosine.

Tyrosine phosphatases can down-regulate the catalytic activity of protein kinases involved in cell proliferation and are therefore thought to be possible anti-cancer proteins. Protein phosphatases with inappropriate activity are also involved in some types of cancer. Because abnormally elevated levels of cell proliferation are associated with receptor and non-receptor protein kinases with unregulated activity, protein phosphatase-catalyzed dephosphorylation of a protein kinase can down-regulate kinase activity and thereby decrease the rate of cell proliferation.

In addition to their role in cellular proliferation, protein phosphatases are thought to be involved in cellular differentiation processes. Cell differentiation occurs in some cells upon nerve growth factor (NGF) or epidermal growth factor (EGF) stimulation. Cellular differentiation is characterized by rapid membrane ruffling, cell flattening, and increases in cell adhesion. Chao, 1992, *Cell* 68:995–997.

Alignment of primary amino acid sequences of known PTPs shows that their catalytic domains share common amino acid sequences. This observation has facilitated efforts of cloning protein phosphatases from multiple organisms and tissues. Probing cDNA libraries with polynucleotides complementary to cDNA encoding protein phosphatase consensus sequences has identified cDNAs resembling protein phosphatase sequences via the polymerase chain reaction (PCR). Some polypeptide molecules encoded by these cDNAs have tyrosine phosphatase activity.

SUMMARY OF THE INVENTION

The present invention relates to nucleic acid molecules encoding a newly identified protein tyrosine phosphatase named PTP20, nucleic acid molecules encoding portions of the fill length protein, nucleic acid vectors harboring such nucleic acid molecules, cells containing such nucleic acid vectors, purified polypeptides encoded by such nucleic acid molecules, antibodies to such proteins and polypeptides, and methods of identifying compounds that bind PTP20 or abrogate its interactions with natural binding partners. Also disclosed are methods for diagnosing abnormal conditions in an organism with PTP20 related molecules or compounds. The nucleic acid molecules, nucleic acid vectors, host cells, polypeptides, and antibodies may be produced using the information provided herein in conjunction with well known and standard techniques used currently in the art.

The present invention is based in part upon the isolation and characterization of nucleic acid molecules encoding a novel protein phosphatase designated PTP20. PTP20 regulates growth factor stimulation of cellular differentiation. PTP20 is thought to be involved in cellular differentiation, as its over-expression in rat pheochromocytoma cells (PC12) is associated with increased rates of differentiation. Various treatments of neural cancers as well as neural damage are thus provided based on the discovery of PTP20 and its role in these disorders.

Thus in a first aspect, the invention features an isolated, enriched, or purified nucleic acid molecule encoding a PTP20 polypeptide.

The term "isolated", in reference to nucleic acid molecules, indicates that a naturally occurring sequence has been removed from its normal cellular environment. Thus, the sequence may be in a cell-free solution or placed in a different cellular environment. The term does not imply that the sequence is the only nucleotide chain present, but that it is essentially free (about 90–95% pure at least) of non-nucleotide material such as chromosomal DNA or proteins.

The term "enriched", in reference to nucleic acid molecules, means that the specific DNA or RNA sequence constitutes a significantly higher fraction (2–5 fold) of the total DNA or RNA present in the cells or solution of interest than in normal or diseased cells or in the cells from which the sequence was taken. A person skilled in the art could enrich a nucleic acid mixture by preferentially reducing the amount of other DNA or RNA present, or preferentially increasing the amount of the specific DNA or RNA, or both. However, nucleic acid molecule enrichment does not imply that there is no other DNA or RNA present, the term only indicates that the relative amount of the sequence of interest has been significantly increased. The term "significantly" qualifies "increased" to indicate that the level of increase is useful to the person performing the recombinant DNA technique, and generally means an increase relative to other nucleic acids of at least 2 fold, or more preferably at least 5 to 10 fold or more. The term also does not imply that there is no DNA or RNA from other sources. Other DNA may, for example, comprise DNA from a yeast or bacterial genome, or a cloning vector. In addition, levels of mRNA may be naturally increased relative to other species of mRNA when working with viral infection or tumor growth techniques. The term "enriched" is meant to cover only those situations in which a person has intervened to elevate the proportion of the desired nucleic acid.

Most methods of recombinant nucleic acid manipulation require that these molecules are in a purified form. The term "purified", in reference to nucleic acid molecules does not require absolute purity (such as a homogeneous preparation); instead, it represents an indication that the sequence is relatively more pure than in its cellular environment (compared to the natural level this level should be at least 2–5 fold greater, e.g., in terms of mg/ml). The claimed DNA molecules obtained from clones could be obtained directly from total DNA or from total RNA. cDNA clones are not naturally occurring, but rather are preferably obtained via manipulation of a partially purified, naturally occurring substance (messenger RNA). The construction of a cDNA library from mRNA involves the creation of a synthetic substance (cDNA). Individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is favored in these techniques.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA that is bound to a membrane. The probe hybridizes (inds) to complementary sequences of cDNA.

The term "complementary" describes two nucleotides that can form multiple favorable interactions with one another. For example, adenine is complementary to thymidine as they can form two hydrogen bonds. Similarly, guanine and cytosine are complementary since they can form three hydrogen bonds. Thus a "complement" of a nucleic acid molecule is a molecule containing adenine instead of thymine, thymine instead of adenine, cytosine instead guanine, and guanine instead of cytosine. Because the complement contains a nucleic acid sequence that forms optimal interactions with the parent nucleic acid molecule, such a complement binds with high affinity to its parent molecule.

The term "hybridize" refers to a method of interacting a nucleic acid molecule (e.g., a nucleic acid probe) with a DNA or RNA molecule in solution or on a solid support, such as cellulose or nitrocellulose. If a nucleic acid probe binds to the DNA or RNA molecule with high affinity, it is said to "hybridize" to the DNA or RNA molecule. As mentioned above, the strength of the interaction between the probe and its target can be assessed by varying the stringency of the hybridization conditions. Various low or high stringency hybridization conditions may be used depending upon the specificity and selectivity desired. Stringency is controlled by varying salt or denaturant concentrations. Those skilled in the art will recognize how such conditions can be varied to vary specificity and selectivity. Under highly stringent hybridization conditions only highly complementary nucleic acid sequences hybridize. Preferably, such conditions prevent hybridization of nucleic acids having one or two mismatches out of 20 contiguous nucleotides.

cDNAs are molecules that may be reverse-transcribed from fragments of message RNA from a genomic source. These fragments form a cDNA library of nucleic acid molecules. cDNA libraries are constructed from natural sources such as mammalian blood, semen, or tissue.

The term "subtractive hybridization" refers to a method similar to cDNA cloning except that cDNA prepared from mRNA in unstimulated cells is added to mRNA in stimulated or different types of cells. cDNA/mRNA can then be precipitated to enrich the mRNA specific to the stimulation signal or different cell type.

The term "PTP20 polypeptide" refers to a polypeptide having an amino acid sequence preferably of at least 400 contiguous amino acids, more preferably of at least 450 contiguous amino acids, or most preferably of at least 453 contiguous amino acids set forth in SEQ ID NO: 7, or is substantially similar to such a sequence, or have substantially similar functional activities such as phosphatase activity or growth or differentiation activity, and may be measured as described herein, e.g. at p. 26, lines 9–25, or p. 29, lines 14–28. A sequence that is substantially similar will preferably have at least 90% identity (more preferably at least 95% and most preferably 99–100% identity) to the amino acid sequence of SEQ ID NO: 7. PTP20 polypeptides preferably have tyrosine phosphatase activity and fragments of the full length PTP20 sequence having such activity may be identified using techniques well known in the art, such as sequence comparisons and assays such as those described in the examples herein.

The term "identity" refers to a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity. Such programs are generally able to achieve maximum alignment by ignoring deletions or additions that would otherwise alter the calculation of the percentage of identity between two sequences.

A preferred embodiment concerns nucleic acid molecules relating to PTP20 enriched, isolated, or purified from a mammalian source. These nucleic acid molecules can be isolated from, among other sources, blood, semen, or tissue.

The term "mammalian" refers to such organisms as, for example, mice, fats, rabbits, goats, monkeys, apes, and preferably humans. Although the PTP20 nucleic acid molecule of SEQ ID NO:1 is isolated from rat cells, current recombinant DNA techniques can readily elucidate a related nucleic acid molecule in human tissue.

Another preferred embodiment concerns an isolated nucleic acid molecule relating to PTP20 that encodes at least twelve contiguous amino acids of the amino acid sequence set forth in SEQ ID NO: 7. Preferably at least 12, 15, 20, 25, 30, 35, 40, 50, 100, 200 or 300 contiguous amino acids of the PTP20 sequence are encoded. This preferred embodiment of the invention is achieved by applying routine recombinant DNA techniques known to those skilled in the art.

Another aspect of the invention features a nucleic acid probe that can detect nucleic acid molecules encoding a PTP20 polypeptide in a sample.

The term "nucleic acid probe" refers to a nucleic acid molecule that is complementary to and can bind a nucleic acid sequence encoding the amino acid sequence substantially similar to that set forth in SEQ ID NO: 7.

By "substantially similar" it is meant a sequence that will preferably have at least 90% identity (more preferably at least 95% and most preferably 99–100%) to the sequence set forth in SEQ ID NO: 1 or SEO ID NO: 7.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

The nucleic acid probe or its complement encodes any one of the amino acid molecules set forth in the invention. Thus the nucleic acid probe can encode at least 12, 75, 90, 105, 120, 150, 200, 250, 300 or 350 contiguous amino acids of the full-length sequence set forth in SEQ ID NO: 7.

The nucleic acid probe can be labeled with a reporter molecule or molecules. The term "reporter molecule" refers to a molecule that is conjugated to the nucleic acid probe or is contained within the nucleic acid probe. The reporter molecule allows the detection of the probe by methods used in the art. Reporter molecules are chosen from, but not limited to; the group consisting of an enzyme, such as a peroxidase, a radioactive element, or an avidin molecule.

A nucleic acid probe, whether labeled or unlabeled, should hybridize to a complement in a sample.

The nucleic acid probe of the present invention can be a nucleic acid molecule encoding a conserved or unique region of amino acids of PTP20. These nucleic acid molecules are useful as hybridization probes to identify and clone additional polypeptides relating to PTP20.

The term "conserved nucleic acid regions", refers to regions present in two or more nucleic acid molecules encoding a PTP20 polypeptide, to which a particular nucleic acid sequence can hybridize under low stringency conditions. Examples of low stringency conditions suitable for screening nucleic acid molecules encoding PTP20 polypeptides are provided in Abe, et al. *J. Biol. Chem.*, 19:13361 (1992) (hereby incorporated by reference herein in its entirety, including any drawings). Preferably, conserved regions differ by no more than 5 out of 20 nucleotides. As mentioned above, protein tyrosine phosphatases share conserved regions in their extracellular and catalytic domains.

The term "unique nucleic acid region" concerns a sequence present in a full length nucleic acid coding for a PTP20 polypeptide that is not present in a sequence coding for any other naturally occurring polypeptide. Such regions preferably comprise 30 or 45 contiguous nucleotides present in the full length nucleic acid sequence encoding a PTP20 polypeptide. In particular, a unique nucleic acid region is preferably of mammalian origin.

Methods for using the probes include detecting the presence or amount of PTP20 RNA in a sample by contacting the sample with a nucleic acid probe under conditions such that hybridization occurs. The nucleic acid duplex formed between the probe and a nucleic acid sequence coding for a PTP20 polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container holding a nucleic acid probe.

In yet another aspect, the invention relates to a nucleic acid vector comprising a nucleic acid molecule encoding a PTP20 polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the PTP20 nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the PTP20 nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

A nucleic acid vector can be useful for identifying natural binding partners of PTP20 polypeptides.

The term "natural binding partners" refers to polypeptides that bind to PTP20 and play a role in propagating a signal in a signal transduction process. The term "binding partner" also refers to a polypeptide that binds to PTP20 within a cellular environment with high affinity. High affinity represents an equilibrium binding constant on the order of $10^{-6}$ M. However, a natural binding partner can also transiently interact with a PTP20 polypeptide and chemically modify it. PTP20 natural binding partners are chosen from a group consisting of, but not limited to, src homology 2 (SH2) (Sadowski, et al, Mol. Cell. Biol. 6:4396, 1986; Pawson and Schlessinger, Curr. Biol. 3:434, 1993) or 3 (SH3) domains (Mayer, et al, Nature 332:272, 1988; Pawson and Schlessinger, Curr. Biol. 3:434, 1993), other phosphoryl tyrosine binding domains, and receptor and non-receptor protein kinases or protein phosphatases.

Methods are readily available in the art for identifying natural binding partners of polypeptides of interest by screening cDNA libraries included in one nucleic acid vector with a nucleic acid molecule encoding the desired polypeptide in another expression construct. Vojtek et al., 1993, *Cell* 74:205–214. These techniques often utilize two halves of a transcription factor, one of which is fused to a polypeptide encoded by the cDNA library, and the other of which is fused to the polypeptide of interest. Interactions between a polypeptide encoded by the cDNA library and the polypeptide of interest are detected when their interaction concomitantly brings together the two halves of the transcription factor and activates a gene that reports the interaction. Any of the nucleic molecules encoding PTP20 polypeptide can be readily incorporated into a nucleic acid vector used in such a screening procedure by utilizing standard recombinant DNA techniques in the art.

Another aspect of the invention relates to a recombinant cell or tissue comprising a nucleic acid molecule encoding a PTP20 polypeptide.

The term "recombinant" refers to an organism that has a new combination of genes or nucleic acid molecules. A new combination of genes or nucleic acid molecules can be introduced to an organism using a wide array of nucleic acid manipulation techniques available to those skilled in the art. The recombinant cell can be a eukaryotic or a prokaryotic organism.

The term "eukaryote" refers to an organism comprised of cells that contain a nucleus. Eukaryotes are differentiated from "prokaryotes" which do not house their genomic DNA inside a nucleus. Prokaryotes include unicellular organisms such as bacteria while eukaryotes are represented by yeast, invertebrates, and vertebrates.

The term "organism" relates to any living being comprised of at least one cell. An organism can be as simple as one eukaryotic cell or as complex as a mammal.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Yet another aspect of the invention features an isolated, enriched, or purified PTP20 polypeptide.

The term "isolated", in reference to a polypeptide, describes a polymer of amino acids conjugated to one another, including polypeptides that are isolated from a natural source or that are synthesized. In certain aspects longer polypeptides are preferred, such as those with most of the contiguous amino acids set forth in SEQ ID NO: 7.

The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

The term "enriched", in reference to a polypeptide, defines a specific amino acid sequence constituting a significantly higher fraction (2–5 fold) of the total of amino acids present in the cells or solution of interest than in normal or diseased cells or in the cells from which the sequence was separated. A person skilled in the art can preferentially reduce the amount of other amino acid sequences present, or preferentially increase the amount of specific amino acid sequences of interest, or both. However, the term "enriched" does not imply that there are no other amino acid sequences present. Enriched simply means the relative amount of the sequence of interest has been significantly increased. The term "significant" indicates that the level of increase is useful to the person making such an increase. The term also means an increase relative to other amino acids of at least 2 fold, or more preferably at least 5 to 10 fold, or even more. The term also does not imply that there are no amino acid sequences from other sources. Other source amino acid sequences may, for example, comprise amino acid sequences from a host organism: "Enriched" is meant to cover only those situations in which a person has intervened to elevate the proportion of the desired amino acid sequence.

The term "purified", in reference to a polypeptide, does not require absolute purity (such as a homogeneous preparation); instead, it represents an indication that the amino acid sequence is relatively more pure than in a cellular environment. The concentration of the preferred amino acid sequence should be at least 2–5 fold greater (in terms of mg/ml) than its concentration in a cellular environment. Purification of at least one order of magnitude, preferably two or three orders, and more preferably four or five orders of magnitude is preferred. The substance is preferably free of contamination, as indicated by purity levels of 90%, 95%, or 99%.

A preferred embodiment relates to a PTP20 polypeptide that is a unique fragment of a PTP20 polypeptide.

The term "unique fragment" refers to a stretch of contiguous amino acids in PTP20 that is of a different sequence than another PTP. At least 12, 15, 20, 25, 30, 35, 40, 50, 100, 150, 200, 250, 300, or 350 contiguous amino acids of the full-length amino acid sequence of PTP20 are unique to PTP20.

The PTP20 polypeptide can be isolated, enriched, or purified from a prokaryotic or eukaryotic recombinant cell. A eukaryotic cell can arise from organisms including mammals and preferably humans. Multiple standard techniques are available to those skilled in the art to facilitate isolation, enrichment, or purification of a polypeptide from recombinant cells. These methods typically include lysing the recombinant cells and separating the polypeptide of interest from the rest of the cell polypeptides, nucleic acids, and fatty acid-based material using standard techniques known in the art.

Another aspect of the invention features an antibody that is monoclonal or polyclonal, or an antibody fragment having specific binding affinity to a PTP20 polypeptide.

Antibodies or antibody fragments are polypeptides which contain regions that can bind other polypeptides. The term "specific binding affinity" describes an antibody that binds to a PTP20 polypeptide with greater affinity than it binds to other polypeptides under specified conditions.

The term "polyclonal" refers to antibodies that are heterogenous populations of antibody molecules derived from the sera of animals immunized with an antigen or an antigenic functional derivative thereof. For the production of polyclonal antibodiwes, various host animals may be immunized by injection with the antigen. Various adjuvants may be used to increase the immunological reponse, depending on the host species.

"Monoclonal antibodies" are substantially homogenous populations of antibodies to a particular antigen. They may be obtained by any techniques which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

Antibodies or antibody fragments having specific binding affinity to a PTP20 polypeptide may be used in methods for detecting the presence and/or amount of a PTP20 polypeptide in a sample by probing the sample with the antibody under conditions suitable for PTP20-antibody immunocomplex formation and detecting the presence and/or amount of the antibody conjugated to the PTP20 polypeptide. Diagnostic kits for performing such methods may be constructed to include antibodies or antibody fragments specific for PTP20 as well as a conjugate of a binding partner of the antibodies or the antibodies themselves.

An antibody or antibody fragment with specific binding affinity to a PTP20 polypeptide can be isolated, enriched, or purified from a prokaryotic or eukaryotic organism. Routine methods known to those skilled in the art enable production of antibodies or antibody fragments, in both prokaryotic and eukaryotic organisms. Purification, enrichment, and isolation of antibodies, which are polypeptide molecules, are described above.

Another aspect of the invention features a hybridoma which produces an antibody having specific binding affinity to a PTP20 polypeptide. A "hybridoma" is an immortalized cell line which is capable of secreting an antibody, for example an antibody with specific binding affinity to PTP20.

Another aspect of the invention features an isolated, enriched, or purified nucleic acid molecule comprising a nucleotide sequence that: (a) encodes a polypeptide having the full length amino acid sequence set forth SEQ ID NO: 7; (b) is the complement of the nucleotide sequence of (a); (c) hybridizes under highly stringent conditions to the nucleotide molecule of (b) and encodes a naturally occurring PTP20 protein; (d) encodes a PTP20 polypeptide having the full length amino acid sequence of the sequence set forth in SEQ ID NO: 7 except that it lacks one or more of the following segments of amino acid residues 1–58, 59–294, or 295–453. (e) is the complement of the nucleotide sequence of (d); (f) encodes a polypeptide having the amino acid sequence set forth in SEQ ID NO: 7 from amino acid residues 1–58, 59–294, or 295–453; (g) is the complement of the nucleotide sequence of (f); or (h) encodes a polypeptide having the full length amino acid sequence set forth in SEQ ID NO: 7 except that it lacks one or more of the domains selected from the group consisting of a N-terminal domain, a catalytic domain, and a C-terminal domain, or (i) is the complement of the nucleotide sequence of (h).

The term "N-terminal domain" refers to a portion of the full length PTP20 amino acid sequence spanning from the amino terminus to the start of the catalytic domain. The N-terminal domain spans amino acid residues 1–58 of the sequence set forth in SEQ ID NO: 7.

The term "catalytic domain" refers to a portion of the PTP20 amino acid molecule that does not contain the N-terminal domain and has catalytic activity. The catalytic domain spans amino acid residues 59–294 of the sequence set forth in SEQ ID NO: 7.

The term "C-terminal domain" refers to a portion of PTP20 that begins at the end of the catalytic domain and ends at thecarboxy terminal amino acid, which is the last amino acid encoded before the stop codon in the nucleic acid sequence. The C-terminal domain spans. amino acid residues 295–453 of the sequence set forth in SEQ ID NO: 7.

Domains are regions of polypeptides which have particular functions. For instance, N-terminal or C-terminal domains of signal transduction proteins can serve functions including, but not limited to, binding molecules that localize the signal transduction molecule to different regions of the cell or binding other signaling molecules directly responsible for propagating a particular cellular signal. Some domains can be expressed separately from the rest of the protein and function by themselves, while others must remain part of the intact protein to retain function. The latter are termed functional regions of proteins and also relate to domains.

Functional regions of PTP20 may be identified by aligning the amino acid sequence of PTP20 with amino acid sequences of other polypeptides with known functional regions. If regions of PTP20 share high amino acid identity with the amino acid sequences of known functional regions, then PTP20 can be determined to contain these functional regions by those skilled in the art. The functional regions can be determined, for example, by using computer programs and sequence information available to those skilled in the art.

Other functional regions of signal transduction molecules that may exist in the PTP20 amino acid sequence include, but are not limited to, proline-rich regions or phosphoryl tyrosine regions. These regions can interact with natural binding partners such as SH2 or SH3 domains of other signal transduction molecules.

In yet another aspect, the invention includes a nucleic acid vector containing a nucleic acid molecule described above.

Another aspect of the invention relates to a recombinant cell or tissue that contains a nucleic acid molecule described above.

In yet another aspect, the invention features a method of identifying compounds capable of modulating PTP20 catalytic activity. This method consists of the following steps: (a) adding a compound to cells containing a PTP20 polypeptide; and (b) detecting a change in the catalytic activity of the PTP20 polypeptide.

The term "modulating" refers to the ability of a compound to alter PTP20 catalytic activity. A modulator preferably activates PTP20 catalytic activity, more preferably activates or inhibits PTP20 catalytic activity depending on the concentration of the compound exposed to PTP20, or most preferably inhibits PTP20 catalytic activity.

The term "compound" includes small organic molecules including, but not limited to, oxindolinones, quinazolines, tyrphostins, quinoxalines, and extracts from natural sources.

The term "a change in catalytic activity", in the context of the invention, defines a method of observing a change in PTP20 catalytic activity in response to adding a compound to cells. The catalytic activity of a PTP20 polypeptide can be detected, for example, by measuring the amount of a substrate, such as p-nitrophenylphosphate, converted to a product, such as p-nitrophenol, with respect to time. Addition of a compound to cells expressing a PTP20 polypeptide may either enhance (activate) or lower (inhibit) the catalytic activity. If a compound lowers PTP20 catalytic activity, the compound is assumed to bind to a PTP20 polypeptide and block the ability of PTP20 to bind and/or turn over a substrate. If a compound enhances PTP20 catalytic activity, the compound is assumed to bind to a PTP20 polypeptide and facilitate the ability of PTP20 to bind and/or turn over a substrate.

The method can utilize any of the molecules disclosed in the invention. These molecules include nucleic acid molecules encoding PTP20 polypeptides, nucleic acid vectors, recombinant cells, polypeptides, or antibodies of the invention.

Another aspect of the invention relates to a method of identifying compounds useful for diagnosis or treatment of an abnormal condition in an organism. The abnormal condition can be associated with an aberration in a signal transduction pathway characterized by an interaction between a PTP20 polypeptide and a natural binding partner. The method comprises the following steps: (a) adding a compound to cells; and (b) detecting whether the compound promotes or disrupts an interaction between a PTP20 polypeptide and a natural binding partner.

The term "abnormal condition" refers to a function in an organism's cells or tissue that deviate from a normal function in the cells or tissue of that organism. In the context of this aspect of the invention, abnormal conditions can be associated with, for example, cell proliferation. Cell proliferative disorders include, but are not limited to, cancers such as fibrotic and mesangial disorders, abnormal angiogenesis and vasculogenesis, slow wound healing rates, psoriasis, diabetes mellitus, and inflammation. Abnormal conditions can also be associated with cell differentiation. Cell differentiation disorders include, but are not limited to, neurodegenerative disorders, slow wound healing rates, and grafting tissue grafting techniques.

The abnormal condition can be diagnosed when the organism's cells exist within the organism or outside of the organism. Cells existing outside the organism can be maintained or grown in cell culture dishes. For cells harbored within the organism, many techniques exist in the art to administer compounds, including (but not limited to) oral, parenteral, dermal, and injection applications. For cells outside of the patient, multiple techniques exist in the art to administer the compounds, including (but not limited to) cell microinjection techniques, transformation techniques, and carrier techniques.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein kinases, receptor and non-receptor protein phosphatases, and transcription factors.

The term "aberration", in conjunction with a signal transduction process, refers to a polypeptide, for example PTP20, that is over- or under-expressed in an organism, mutated such that its catalytic activity is lower or higher than wild-type polypeptide, mutated such that it can no longer interact with a binding partner, is no longer modified by another protein kinase or protein phosphatase, or no longer interacts with a binding partner.

The term "interaction" defines the complex formed between a PTP20 polypeptide and a natural binding partner. Compounds can bind to either the PTP20 polypeptide or the natural binding partner and disrupt the interaction between the two molecules.

The term "promote or disrupt the abnormal interaction" refers to a method that can be accomplished by administering a compound to cells or tissues in an organism. A compound can promote an interaction between PTP20 and natural binding partners by forming favorable interactions with multiple atoms at the complex interface. Alternatively, a compound can inhibit an interaction between a protein kinase and natural binding partners by compromising favorable interactions formed between atoms at the complex interface.

Methods of detecting the ability of a compound to disrupt or enhance an interaction between PTP20 and a natural binding partner exist in the art. These methods include, but are not limited to, determining the effect of the compound upon the catalytic activity of a PTP20 polypeptide, the phosphorylation state of the PTP20 polypeptide or a natural binding partner, the ability of PTP20 to bind a natural binding partner, or a difference in a cell morphology. Differences in cell morphology include growth rates and differentiation rates of cells. These phenomena are simply measured by methods in the art. These methods typically involve observing the number of cells or the appearance of cells under a microscope with respect to time (for example, days).

The method can be performed in vitro as well as in vivo. In vivo applications include introducing a group of cells to an organism and then determining the effect of a compound administered to the organism on the state of the organism as well as the introduced cells. The art contains multiple methods of introducing a group of cells to an organism as well as methods of administering a compounds to an organism. The organism is preferably an animal such as a frog, mouse, rat, rabbit, monkey, or ape, and also a human.

Another aspect of the invention relates to a method of diagnosing an abnormal condition associated with cell proliferation or cell differentiation in an organism. The abnormal condition can be associated with an aberration in a signal transduction pathway characterized by an interaction between a PTP20 polypeptide and a natural binding partner. The method comprises the step of detecting an abnormal interaction.

The term "detecting an abnormal interaction" defines a method of identifying a PTP20 molecule with an aberration in its activity. Detection is accomplished by using an antibody or antibody fragment of the invention, a nucleic acid probe of the invention, or a compound of the invention.

Techniques used in the art that incorporate this method include in vitro, in vivo, and in situ hybridization techniques. These techniques utilize nucleic acid probes of the invention.

A preferred embodiment of the invention is the diagnosis method relating to an organism that is a mammal.

The summary of the invention described above is not limiting and other features and advantages of the invention will be apparent from the following detailed description of the invention, and from the claims.

DETAILED DESCRIPTION OF THE INVENTION

The present invention is based in part upon the isolation and characterization of nucleic acid molecules encoding a novel protein tyrosine phosphatase designated PTP20. The invention relates to nucleic acid molecules encoding portions of the PTP20 polypeptide, nucleic acid molecules encoding at least one PTP20 functional portion, nucleic acid vectors harboring such nucleic acid molecules, recombinant cells containing such nucleic acid vectors, purified polypeptides encoded by such nucleic acid molecules, antibodies to such polypeptides, and methods of identifying compounds that bind PTP20 or modulate its interactions with natural binding partners. Also disclosed are methods for diagnosing abnormal conditions in an organism with PTP20 related molecules or compounds.

The open reading frame of the full-length PTP20 nucleic acid molecule encodes a protein of 453 amino acids with a predicted molecular weight of approximately 50 kDa. Hydropathy analysis (see Kyte and Doolittle, 1982, *J. Mol. Bio.* 157:105–132) indicates that PTP20 contains no hydrophobic segments appropriate for signal peptide or transmembrane domains and therefore PTP20 is most likely an intracellular protein. The transcripts corresponding to nearly the same size of the full length cDNA are detected in several tissues including brain, liver, lung, spleen, skeletal muscle, kidney, and testis. The tissues may come from rats or other mammals.

The catalytic domain is located near the predicted amino terminus between amino acids 58 and 283. The catalytic domain of PTP20 may be homologous to the PTP-PEST-family phosphatases, such as human and rat PTP-PESTs and PEP-PTP. Takekawa et al., 1992, *Biochem. Biophys. Res. Commun.* 189:1223–1230; Yang et al., 1993, *J. Biol. Chem.* 268:6622–6628; Matthews et al., 1992, *Mol. Cell. Biol.* 12:2396–2405. Proline, glutamate, serine, and threonine residues (PEST) are enriched in the PEST-motif sequence, which is not arranged in any specified consensus sequence. Rechsteiner and Rogers, 1996, *TIBS* 21:267–271. PTP20 may have a PEST sequence between amino acids 285 and 453, suggesting that PTP20 may be a member of the PTP-PEST family.

Experimental results implicate PTP20 as an essential agent involved in a growth factor stimulated cellular differentiation signal transduction pathway. Although most cells have already differentiated in adults, activators of PTP20 might cause differentiation instead of proliferation of cellular tumors and therefore act as anti-cancer therapeutics. In addition, inhibitors of PTP20 might be useful for treating neural injuries by delaying the differentiation of transplanted neuronal stem cells until they are firmly grafted.

Various other features and aspects of the invention are: nucleic acid molecules encoding a PTP20 polypeptide; nucleic acid probes for the detection of PTP20; a probe-based method and kit for detecting PTP20 messages in other organisms; DNA constructs comprising a PTP20 nucleic acid molecule and cells containing these constructs; purified PTP20 polypeptides; PTP20 antibodies and hybridomas; antibody-based methods and kits for detecting PTP20; identification of agents; isolation of compounds which interact with a PTP20 polypeptide; compositions of compounds that interact with PTP20 and PTP20 molecules; pharmaceutical formulations and modes of administration; derivatives of complexes; antibodies to complexes; disruption of PTP20 protein complexes; purification and production of complexes; transgenic animals containing PTP20 nucleic acid constructs; antisense and ribozyme approaches, gene therapy; and evaluation of disorders. One skilled in the art appreciates that any modifications made to a complex can be manifested in a modification of any of the molecules in that complex. Thus, the invention includes any modifications to nucleic acid molecules, polypeptides, antibodies, or compounds in a complex. All of these aspects and features are explained in detail with respect to PYK-2 in PCT publication WO 96/18738, which is incorporated herein by reference in its entirety, including any drawings. Those skilled in the art will readily appreciate that such descriptions can be easily adapted to PTP20 as well, and are equally applicable to the present invention.

EXAMPLES

The examples below are non-limiting and are merely representative of various aspects and features of the present invention. The examples below demonstrate the isolation, and characterization of the novel protein PTP20.

Example 1

PCR Amplification and Cloning

In order to identify novel PTP genes involved in differentiation of PC12 cells, which are available from ATCC (CRL1721), reverse transcriptase-PCR amplification was performed using poly(A)$^+$RNA from both undifferentiated and differentiated PC12 cells as a template and degenerate primers that were deduced from highly conserved amino acid sequences within the PTP catalytic domain. This reaction gave specific products of 350–400 bp. These fragments were isolated, cloned and sequenced. PCR clone number 20 (PTP20) exhibited sequence similarities but was not identical to any previously known PTPs. Using the PTP20 PCR-generated cDNA fragment as a probe, a full length cDNA clone was isolated from a PC12 cDNA library and characterized by sequence analysis.

Degenerate oligonucleotide sense and antisense primers were based on consensus sequences for two highly conserved amino acid stretches within the catalytic domains of PTPs: FWXMXW (SEQ ID NO:2) and HCSAG(S/I/V)G (SEQ ID NO:3). Random-primed cDNA (up to 50 ng) from PC12 cell RNA was used as a template for PCR. Both sense and antisense primers were added to a 100 mL reaction mixture containing 20 mM Tris-HCl (pH 8.4), 50 mM KCl, 2.5 mM $MgCl_2$, 0.01% BSA, all four dNTPs (each at 200 mM), 1 unit of Taq polymerase (Boehringer Mannheim) and template cDNA. Thirty-five cycles were carried out on a thermal cycler; each cycle involved incubation at 94° C. for 1 min, at 42° C. for 1 min and 72° C. for 1 min. The PCR products were separated on a 1.5% agarose gel. Fragments of 350–400 bp were excised, subcloned into pBluescript KS(+) and sequenced.

The PTP20 PCR fragment was isolated, radioactively labeled by random priming, and used to screen $1 \times 10^6$ plaques from a PC12 cDNA library which had been made using a pool of poly(A)$^+$ RNA from both undifferentiated and differentiated PC12 cells, and a ZAPII synthesis kit (Stratagene). Hybridization was performed in a solution containing 50% (v/v) formamide, 5×SSC, 5×Denhardt solution, 0.05M sodium phosphate, 1 mM $NaH_2PO_4$, 1 mM $Na_4P_2O_7$, 0.1 mM ATP, 5 mg salmon sperm DNA at 42° C. for 20 h. Washing was repeated three times with 2×SSC/0.1% SDS for 20 min at 42° C. Six positive clones were obtained and plaque-purified by secondary screening. Positive clones were rescued according to the manufacturer's instruction and sequenced in both directions.

The 2226 bp cDNA clone of PTP20 contained an open reading frame of 1359 bp preceded by 27 base pairs of 5'-non-coding region and 840 base pairs of 3'-non-coding region. The 3'-non-coding region contained the polyadenylation signal sequence AATAAA. The open reading frame encoded a protein of 453 amino acids with a predicted molecular weight of approximately 50 kDa.

Example 2

PCR Amplification and Cloning Using Human Cells

PTP genes involved in differentiation of human cells could be identified by reverse transcriptase-PCR amplification performed using poly(A)$^+$RNA from both undifferentiated and differentiated human cells as a template and degenerate primers that are deduced from highly conserved amino acid sequences within the PTP catalytic domain. The human cells could be isolated from various different tissues. This reaction gives specific products of different lengths. These fragments are isolated, cloned and sequenced. A PCR clone (PTP20) exhibits sequence similarities but is not identical to any previously known PTPs. Using the PTP20 PCR-generated cDNA fragment as a probe, a full length cDNA clone is isolated from a PC12 cDNA library and characterized by sequence analysis.

Degenerate oligonucleotide sense and antisense primers are based on consensus sequences for two highly conserved amino acid stretches within the catalytic domains of PTPs: FWXMXW and HCSAG(S/I/V)G. Random-primed cDNA (up to 50 ng) from PC12 cell RNA are used as a template for PCR. Both sense and antisense primers are added to a 100 mL reaction mixture containing 20 mM Tris-HCl (pH 8.4), 50 mM KCl, 2.5 mM $MgCl_2$, 0.01% BSA, all four dNTPs (each at 200 mM), 1 unit of Taq polymerase (Boehringer Mannheim) and template cDNA. Thirty-five cycles are carried out on a thermal cycler; each cycle involves incubation at 94° C. for 1 min, at 42° C. for 1 min and 72° C. for 1 min. The PCR products are separated on a 1.5% agarose gel. Fragments of 350–400 bp are excised, subcloned into pBluescript KS(+) and sequenced.

The PTP20 PCR fragment is isolated, radioactively labeled by random priming, and used to screen $1 \times 10^6$ plaques from a PC12 cDNA library which has been made using a pool of poly(A)$^+$ RNA from both undifferentiated and differentiated PC12 cells, and a ZAPII synthesis kit (Stratagene). Hybridization is performed in a solution containing 50% (v/v) formamide, 5×SSC, 5×Denhardt solution, 0.05M sodium phosphate, 1 mM $NaH_2PO_4$, 1 mM $Na_4P_2O_7$, 0.1 mM ATP, 5 mg salmon sperm DNA at 42° C. for 20 h. Washing is repeated three times with 2×SSC/0.1% SDS for 20 min at 42° C. Six positive clones are obtained and plaque-purified by secondary screening. Positive clones are rescued according to the manufacturer's instruction and sequenced in both directions.

Example 3

PTP20 Message in Response to NGF

To elucidate the role of PTP20 in the differentiation process of PC12 cells, Northern blot analysis was used to examine the expression pattern of PTP20 mRNA in PC12 cells treated with NGF for three or six days. Untreated PC12 cells exhibited a 2.3 kb PTP20 mRNA transcript. Following 3 days of NGF treatment, a 1.5-fold increase in the amount of transcript was observed. Another 3 days of NGF treatment caused a 2.4-fold increase as compared to untreated cells. In addition to the predominant 2.3 kb transcript, a faint band with 1.5 kb in size was also detected which also increased in abundance as NGF treatment continued. The expression pattern of PTP20 mRNA suggested that PTP20 might play a role during NGF-induced PC12 differentiation.

Northern blot analyses were carried out according to well established protocols. RNA was extracted from PC12 cells by acid guanidinium isothiocyanate-phenol-chloroform method. Chomczynski and Sacci, 1987, *Anal. Biochem.* 162:156–159. Poly(A)$^+$RNA was isolated with oligo(dT) Sepharose (Stratagene) column chromatography according to the manufacturer's instruction. Two micrograms of poly (A)$^+$RNA was electrophoresed in a formaldehyde/1.0% agarose gel, blotted to a nitrocellulose membrane filter, and hybridizes to $^{32}$P-labeled full length PTP20 cDNA as a probe.

Example 4

PTP20 is Implicated in a Cellular Differentiation Signal Transduction Pathway

To further elucidate the function of PTP20 in cellular differentiation, PC12 cells were stably transfected with the PTP20 cDNA mammalian expression construct.

The following method was utilized to stably transfect cells with a gene encoding PTP20. Rat pheochromocytoma cells (PC12) were cultured in Dulbecco's modified Eagle's medium (DMEM) containing high glucose (4.5 g/liter) supplemented with 10% heat-inactivated horse serum (HS) and fetal calf serum (FCS). $5 \times 10^5$ cells per 60 mm dish were incubated overnight in 4 mL of growth medium. The following day, the dish was washed once with serum-free medium and then incubated with a Lipofectin (5 mL)-DNA (2 mg) mixture for 6 h. After 48 h, selection started in growth medium containing 500 mg/mL G418 (GIBCO BRL). Following 5 weeks of selection, discrete colonies were subcloned and expanded.

From seven stably transfected clonal cell lines, three independent clones showed high levels of PTP20 expression as assessed by Western blotting. In parental PC12 cells, endogenous PTP20 protein was beneath detection with the antibody. These three independent clones appeared morphologically similar to parental PC12 cells. However, following NGF treatment (50 ng/mL), all three clones showed accelerated neurite outgrowth, with 20 to 40% of the cells expressing neurites of more than two cell bodies in length at day 1 and more than 70% of the cells expressing such neurites at day 3. In contrast, the parental PC12 cells showed less than 5% of the cells with neurites of two cell bodies in length at day 1 and 47% at day 3. At day 4 following NGF treatment, more than 70% of both parental PC12 cells and PTP-PC12 cells expressed neurite outgrowth, however, the neurite length and the abundance of neurites in PTP-PC12 cells appeared longer and larger than those of parental PC12 cells. In addition, PTP-PC12 cells responded to lower concentrations of NGF than did parental PC12 cells. This suggests that NGF-induced differentiation was promoted by the expression of PTP20.

Example 5

Production of Functionally Active PTP20

To confirm that PTP20 encodes a functionally active PTPs, Rat-1 fibroblast cells were transiently transfected with mammalian expression constructs encoding either PTP20 or a Cys to Ser mutant of PTP20. Cell lysates were prepared and protein concentrations were determined. The expression level of both wild type and catalytically inactive mutant PTP20 was confirmed by Western blotting with anti-PTP-PEST antibodies. Cross-reactivity with non-specific proteins was not detected as evidenced by lack of a signal in control reactions. Nearly equivalent amounts of expressed protein were detected. The size of the detected protein was 50 kDa which is consistent with the predicted molecular weight of PTP20. For protein tyrosine phosphatase activity, equivalent amounts of protein from the transfected Rat-1 cell lysates were tested using p-nitrophenylphosphate as a substrate. Lysates from transfected cells exhibited an approximately 2.5-fold higher PTP activity over those from control cells, whereas only basal levels of PTPase activity were detected in lysates from cells transfected with a construct encoding a catalytically inactive mutant of PTP20. These results indicate that full length PTP20 cDNA encodes a functionally active PTP.

The insert of PTP20 was excised with EcoRI digestion and integrated into an expression vector, pcDNA3 (Invitrogen) which had been digested with the same restriction enzyme. The direction of the insert in the plasmid was confirmed by restriction mapping. Rat-1 cells were transfected with the plasmid (2 mg/1×10$^6$ cells) by using Lipofectin (GIBCO BRL). After 48 h of culturing, the cells were washed with PBS and then lysed with lysis buffer [50 mM HEPES, pH 7.5, containing 150 mM NaCl, 1 mM EDTA, 10% (v/v) glycerol, 1% (v/v) Triton X-100, 1 mM phenylmethylsulfonyl fluoride, 1 mM sodium orthovanadate, 10 mg/mL aprotinin]. Protein concentrations of cell lysates were measured with a protein assay kit (Bio-Rad) using bovine serum albumin as a standard. Equivalent amounts of protein were used for Western blot analyses and phosphatase activity assay.

The PTP20 mutant containing a cysteine to serine alteration at position 229 was generated using an oligonucleotide primer, CTCTGTGTCCACAGCAGTGCTGGCTGT (SEQ ID NO:4). Kunkel, 1985, *Proc. Natl. Acad. Sci. USA* 82:488–492. The mutation was confirmed by DNA sequencing.

For Western blot analysis, cells were first lysed in lysis buffer. To assess PTP20 expression, equivalent amounts of protein in the cell lysates were separated by 10% SDS-PAGE and electrophoretically transferred to nitrocellulose membranes. The membranes were first incubated with rabbit anti-PTP-PEST antibodies, and then a peroxidase-coupled goat anti-rabbit secondary antibody (BioRad) was added, followed by an enhanced chemiluminescence (ECL) substrate (Amersham) reaction. The substrate reaction was detected on a X-ray film (Amersham). The anti-PTP-PEST antibody was raised against the C-terminal 56 amino acids of human PTP-PEST (Takekawa et al., 1992, *Biochem. Biophys. Res. Commun.* 189:1223–1230) which was expressed as a GST fusion protein.

Phosphatase activity of PTP20 was assayed in a 200 mL solution containing 25 mM MES (2-[N-morpholino] ethanesulfonic acid), pH 5.5, 1.6 mM DTT, 10 mM p-nitrophenylphosphate as a substrate and 50 mg protein of cell lysate at 37° C. for 30 min. The reaction was stopped by the addition of 100 ML of 1N NaOH, and the absorbance was measured at 405 nm.

Example 6

PTP20 Specifically Dephosphorylates EGF Receptor, Thereby Triggering NGF-Induced Differentiation of PC12 Cells Materials and Methods
Construction of Plasmids pUHD15-1neo contains the tetracycline-controlled transactivator (tTA) coding sequence driven by the human cytomega virus (CMV) promoter/enhancer (Gossen, M. et al., (1992) *Proc. Natl. Acad. Sci. USA*, 89, 5547–5551). pUHD10-3 contains the PhCMV*-1 followed by a multiple cloning sequence as described in the art (Gossen et al. 1992). In this study, 6 histidine residues were tagged at the N-terminus of PTP20 wild-type (wt) or catalytically inactive mutant (C/S mutant) by PCR amplification with primers as follows; sense primer: 5'-ATG AAT TCG CCA CCA TGC ATC ACC ATC ACC ATC ACA GTC GCC AAT CGG ACC TAG TGA GG-3' (SEQ ID NO:5) and antisense primer: 5'-ATC TCG AGT TAC ACC CGT GTC CAC TCC GCT GGA GGA TC-3' (SEQ ID NO:6). After PCR amplification, the products were subcloned EcoRI and XbaI sites into pBluescript KS(+) (Stratagene) and sequenced. Then, the products were ligated into pUHD10-3 via the same sites. By transient expression in 293 cells, histidine-tagged PTP20 exhibited indistinguishable PTPase activity toward p-nitrophenyl phosphate from that of native PTP20.
Establishment of Cell Lines PC12 cells which stably express tTA were produced by transfecting 2 μg of pUHD15-1neo with 5 μL of Lipofectin (Life Technologies, Inc.) according to the manufacturer's instruction. Following 4 weeks of selection, cells resistant to 500 μg/mL G418 were cloned and tested for tTA expression by an assay for the transient expression of the β-galactosidase gene in pUHD10-3 (pUHD-gal). In this assay, 2 μg of pUHD-gal was transfected into 5×10$^5$ cells, which had been cultured overnight in the presence or absence of tetracycline (2 μg/mL), using 5 μL of Lipofectin for 6 h. Then the cells were split into two 6-cm dishes in the presence or absence of tetracycline (2 μg/mL) and then cultured for another 48 h. β-galactosidase assays were done using o-nitrophenyl-β-D-galactopyranoside as a substrate. Clone 15-1#5 which showed the highest induction of β-galactosidase activity was selected and used for further transfection of PTP20. The stable transfection of pUHD-PTP20 wt or pUHD-PTP20 C/S into tTA-expressing clone 15-1#5 was performed with Lipofectin as described above.

Two micrograms of pUHD-PTP20 wt or pUHD-PTP20 C/S was transfected into host cells with 0.2 μg of pSV2-hph which contains the hygromycin-resistant gene driven by rous sarcoma virus promoter. Cells were selected with 200 μg/mL hygromycin B (Boehringer Mannheim). Colonies were cloned, expanded and further analysed.

Immunoblotting

Expression of PTP20 was assessed as described previously using anti-PTP-PEST antibody (Aoki et al., (1996) *J. Biol. Chem.*, 271, 294422–29426). To perform co-precipitation experiments for EGF receptor or histidine-tagged PTP20, precleared lysate was incubated with Lentil Sepharose or Ni-NTA agarose (QIAGEN), respectively. Immunoprecipitation of NGF receptor and SHC was carried out essentially as described in the art (Obermeier et al., (1993) *J. Biol. Chem.*, 268, 22963–22966). After extensive washing, the precipitates were separated by SDS-PAGE followed by blotting onto nitrocellulose membrane (Amersham). The blots were incubated with 4G10(UBI) followed by incubation with peroxidase-conjugated goat anti-mouse immunoglobulin. The ECL system (Amersham) was used to visualize proteins recognized by the antibodies. After stripping antibodies off the blots, the procedures were repeated with other antibodies.

Neurite Outgrowth

Prior to experiments, cells were cultured in DMEM containing 10% horse serum (HS) and 5% fetal calf serum (FCS) for 48 h in the presence or absence of tetracycline for the expression of PTP20. Then, cells were inoculated into 6-well plates at a density of $0.5–1.0\times10^4$ cells per well, cultured in the same medium for 1 day, and the cell culture medium was changed to DMEM containing 1% HS, 0.5% FCS and human βNGF (Boehringer Mannheim) in the presence or absence of tetracycline as indicated (Day 0). At indicated days, 100 to 200 cells were counted under microscopy and scored as the expression of neurite longer than one cell body.

[$^3$H]thymidine Incorporation Assay

Prior to experiments, cells were cultured in DMEM containing 10% HS and 5% FCS for 48 h in the presence or absence of tetracycline. Then, cells were plated at $1\times10^5$ cells per mL in 0.5 mL of DMEM containing 0.5% HS and 0.25% FCS in 24-well plates. After 2 days, the medium was replaced with 0.5 mL of DMEM containing 10% HS and 5% FCS, EGF (50 ng/mL), or NGF (50 ng/mL) and incubated for 18 h. Then, 0.8 μCi of [$^3$H]thymidine (Amersham) per ml was added, and the incubation was prolonged for 4 h. Cells were then washed with ice-cold 5% trichloroacetic acid. Insoluble material was harvested and quantified in the presence of liquid scintillator.

Proliferation Assay

Prior to experiments, cells were cultured in DMEM containing 10% HS and 5% FCS for 48 h in the presence or absence of tetracycline. Then, $5\times10^3$ cells per well of 96 well plate were inoculated and cultured in the same medium in the presence or absence of tetracycline. At indicated days, 10 μL of cell proliferation reagent WST-1 solution (Boehringer Mannheim) was directly added to the culture medium and further incubated for 4 h at 37° C. The absorbance at 420 nm was determined with ELISA reader.

MAP Kinase Assay

Soluble cellular lysates prepared in lysis buffer plus phosphatase and protease inhibitors were adjusted to equal protein concentrations and incubated with anti-ERK2 antiserum (Santa Cruz) and Protein A-Sepharose (Pharmacia) for 2 h at 4° C. MAP kinase reactions were performed as described in the art (Traverse et al., (1992) *Biochem. J.*, 288, 351–355) with slight modifications using myelin basic protein as a substrate, after which the samples were separated by SDS-polyacrylamide gel electrophoresis on a 15% polyacrylamide gel. Kinase activity was determined by analysing the dried gel with a PhosphoImager (Fuji Film).

Results

Selection of PTP20-Expressing Clones

Previously it had been observed that PC12 cell clones over-expressing PTP20 grew more slowly than parental PC12 cells, suggesting that the PTPase interfered with cell proliferation signals. To clarify this, tetracycline-controlled system (Gossen et al., 1992) was employed under the conditions that would express the PTP20 gene-in PC12 cells. After establishment of a tetracycline-controlled trans-activator (tTA) cell line, which exhibited low background expression of a β-galactosidase reporter gene and approximately 30 fold induction after tetracycline (Tet) removal, lines that overexpressed PTP20 upon release of Tet expression were generated.

Following transfection with either pUHD-PTP20 wt or pUHD-PTP20 C/S plus hygromycin resistant plasmid into the 15-1#5 clone, 18 clones each resistant to hygromycin B were isolated and analysed by Western blotting using anti-PTP-PEST antibodies. Three clones out of 18 displayed high expression of PTP20 wt and another 3 displayed high expression of C/S mutant when the clones were cultured in the absence of tetracycline, whereas nearly no PTP20 was detected in the presence of tetracycline. On the same blots, nearly the same amount of PTP1B was detected, indicating that the difference in the amount of PTP20 was not due to misloading the samples or other experimental errors. In control cells which had been transfected with empty pUHD10-3 and pSV-hph, the expression of PTP20 wt and C/S mutant was undetectable with antibody used. Examination of various induction times in Tet-free cell culture medium indicated that for maximal expression at least 48 h incubation was needed. Wild-type and C/S mutant clones showed normal morphology indistinguishable from that of native PC12 cells.

The tetracycline-controlled gene expression system allows quantitatively controlled expression of a target gene by the addition or removal of tetracycline (Yin et al., (1995) *Cancer Res.*, 55, 4922–4928). In our PC12 system, the expression of PTP20 wt and C/S mutant was well controlled in a tetracycline concentration-dependent manner whereas the amount of endogenous PTP1B on the same blot was unaffected. Densitometeric analysis showed that expression of PTP20 wt and C/S mutant was reduced by 72% and 82%, respectively, by increasing the amount of tetracycline from 0 to 0.1 μg/mL.

Effect of PTP20 Wild-Type and C/S Mutant Overexpression on Differentiation and Proliferation of PC12 Cells It has been shown that overexpression of PTP20 resulted in accelerated NGF-induced differentiation of PC12 cells (Aoki et al., 1996). This was confirmed with the clone 4 of PTP20 wt. Overexpression of PTP20 wt by removal of tetracycline from the cell culture medium caused rapid differentiation, in which more than 80% of cells expressed neurites 2 days after NGF treatment. Furthermore, the addition of tetracycline (0.1 μg/mL) reduced the effect to about 50%. This level was still much higher than that in the cells exposed to tetracycline with expression levels that were not detectable with the Ab used.

In contrast, induction of PTP20 C/S overexpression by removal of tetracycline suppressed the NGF-induced differentiation of PC12 cells. Only 30% of cells expressed neurites even after 4 days of NGF treatment. This effect was decreased by the addition of tetracycline (0.1 μg/mL). Control cells exhibited nearly the same extent of neurite outgrowth, independent of the amount of tetracycline added to the cell culture medium while EGF had no effect on neurite outgrowth of cells expressing either PTP20 wt or C/S mutant.

EGF and NGF have opposing effects on PC12 cells. EGF as a mitogen stimulates the proliferation of PC12 cells, whereas NGF induces differentiation. As mentioned above, PTP20 wt stimulated the NGF-induced differentiation and preliminary data showed that overexpression of the PTP20 wt resulted in the inhibition of proliferation in serum-supplemented medium. This was clearly demonstrated using the tetracycline-controlled gene expression system. Overexpression of PTP20 wt resulted in approximately 50% reduction in [$^3$H]-thymidine incorporation of the PC12 cells upon serum or EGF stimulation, which was recovered by the addition of tetracycline (0.1 μg/mL). On the other hand, overexpression of PTP20 C/S mutant significantly accelerated the [$^3$H]-thymidine incorporation. These were well consistent with proliferation assay of PC12 cells grown in the serum-containing medium. Overexpression of PTP20 wt caused dramatic reduction in proliferation of the cells, whereas PTP20 C/S mutant slightly but significantly accelerated the growth of the cells.

Effect of Overexpression of PTP20 Wild-Type and C/S Mutant on MAP Kinase Activity upon EGF or NGF Stimulation In PC12 cells, both EGF and NGF activate the p42 and p44 isoforms of MAP kinase. To relate the effects of overexpression of PTP20 wt and C/S mutant on NGF-induced differentiation and mitogen-promoted proliferation, the time course of MAP kinase activity was determined. Consistent with the above data, overexpression of PTP20 wt by removal of tetracycline resulted in higher and sustained MAP kinase activation upon NGF stimulation leading to the accelerated differentiation. This effect was diminished by the addition of tetracycline. In contrast, EGF-treated MAP kinase activation was inhibited by overexpressing PTP20 wt. This was comparable to the data that overexpression of v-Crk caused sustained MAP kinase activation leading to neurite outgrowth upon EGF stimulation (Hempstead et al., (1994) *Mol. Cell. Biol.*, 14, 1964–1971). On the other hand, overexpression of PTP20 C/S mutant caused inhibition or promotion of MAP kinase activation upon NGF or EGF stimulation, respectively. These data suggest that PTP20 inhibit the proliferation of PC12 cells, allowing the cells to lead to accelerated NGF-induced differentiation.

Effect of Overexpression of PTP20 Wild-Type or C/S Mutant on Cellular Tyrosine Phosphorylation To investigate the effect of overexpression of PTP20 wt or C/S mutant on cellular tyrosine phosphorylation, PC12 cells overexpressing either PTP20 wt or C/S mutant upon removal of tetracycline were stimulated with either EGF or NGF. When PTP20 wt was overexpressed, dramatic reduction in tyrosine phosphorylation was observed upon EGF stimulation. This was further investigated by precipitating specific molecules upon ligand stimulation. Overexpression of PTP20 wt resulted in dramatic dephosphorylation of EGF receptor and that tyrosine phosphorylated proteins with molecular masses of 130 kDa and 50 kDa were brought down with EGF receptor upon EGF stimulation only when PTP20 C/S mutant was overexpressed. 50 kDa protein was shown to be PTP20 C/S mutant by Western blotting using anti-PTP-PEST antibody. To confirm this, lysate was precipitated with Ni-TNA-agarose, which is known to associate specifically with histidine residues. Only PTP20 C/S mutant became tyrosine phosphorylated and EGF receptor and 130 kDa protein were co-precipitated. So far the 130 kDa protein has not been identified. Tyrosine phosphorylation level of SHC was also diminished by overexpression of PTP20 wt upon removal of tetracycline from the cell culture medium. In contrast, overexpression of PTP20 wt or C/S mutant did not seem to influence the tyrosine phosphorylation level of NGF receptor and SHC upon NGF stimulation and no physical association between NGF receptor and PTP20 wt or C/S mutant was observed.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. An isolated, enriched or purified nucleic acid molecule encoding a PTP20 polypeptide, wherein said polypeptide comprises at least 100 contiguous amino acids of the amino acid sequence set forth in SEQ ID NO:7 and has tyrosine phosphatase activity.

2. The nucleic acid molecule of claim 1, wherein said nucleic acid molecule is isolated, enriched, or purified from a mammal.

3. A nucleic acid vector comprising a nucleic acid molecule encoding a PTP20 polypeptide and a promoter effective to initiate transcription in a host cell, wherein said polypeptide comprises at least 100 continuous amino acids of the amino acid sequence set forth in SEQ ID NO:7 and has tyrosine phosphatase activity.

4. A recombinant cell or tissue comprising a nucleic acid molecule encoding a PTP20 polypeptide, wherein said polypeptide comprises at least 100 contiguous amino acids of the amino acid sequence set forth in SEQ ID NO:7 and has tyrosine phosphatase activity.

5. An isolated, enriched, or purified nucleic acid molecule comprising a nucleotide sequence that encodes a polypeptide having the full length amino acid sequence set forth SEQ ID NO: 7.

6. A nucleic acid vector comprising a nucleic acid molecule of claim 5.

7. A recombinant cell or tissue comprising a nucleic acid molecule of claim 5.

8. The nucleic acid molecule of claim 1, wherein said polypeptide comprises at least 200 contiguous amino acids of the amino acid sequence set forth in SEQ ID NO:7.

9. The nucleic acid molecule of claim 1, wherein said polypeptide comprises at least 300 contiguous amino acids of the amino acid sequence set forth in SEQ ID NO:7.

10. The nucleic acid molecule of claim 1, wherein said polypeptide comprises at least 400 contiguous amino acids of the amino acid sequence set forth in SEQ ID NO:7.

11. An isolated, enriched, or purified nucleic acid molecule that is the complement of the nucleotide sequence of claim 5.

12. The isolated, enriched, or purified nucleic acid molecule of claim 5, except that it lacks at least one, but not all, of the following segments of amino acid residues 1–58, 59–294 and 295–453.

13. An isolated, enriched, or purified nucleic acid molecule that is the complement of the nucleotide sequence of claim 12.

14. An isolated, enriched, or purified nucleic acid molecule comprising a nucleotide sequence that encodes a polypeptide having the amino acid sequence set forth in SEQ ID NO: 7 from amino acid residues 1–58, 59–294, or 295–453.

15. An isolated, enriched, or purified nucleic acid molecule that is the complement of the nucleotide sequence of claim 14.

16. The isolated, enriched, or purified nucleic acid molecule of claim 5, except that it lacks at least one, but not all, of the domains selected from the group consisting of a N-terminal domain, a catalytic domain, and a C-terminal domain.

17. An isolated, enriched, or purified nucleic acid molecule that is the complement of the nucleotide sequence of claim 16.

* * * * *